United States Patent [19]

Kramer

[11] 4,357,482
[45] Nov. 2, 1982

[54] AMINOALKYL ADAMANTANE CATALYZED PARAFFIN-OLEFIN ALKYLATION

[75] Inventor: George M. Kramer, Berkeley Heights, N.J.

[73] Assignee: Exxon Research and Engineering Co., Florham Park, N.J.

[21] Appl. No.: 298,120

[22] Filed: Aug. 31, 1981

[51] Int. Cl.³ .............................................. C07C 2/58
[52] U.S. Cl. .................................... 585/724; 585/725; 585/726; 585/727; 585/728; 585/729; 585/730; 585/731; 585/732
[58] Field of Search ............... 585/724, 725, 726, 727, 585/728, 729, 730, 731, 732

[56] References Cited

U.S. PATENT DOCUMENTS

| | | | |
|---|---|---|---|
| 2,965,693 | 12/1960 | Kramer | 585/728 |
| 3,231,633 | 1/1966 | Kramer | 585/723 |
| 3,324,196 | 6/1967 | Kramer et al. | 585/725 |
| 3,382,288 | 5/1968 | Schneider | 585/352 |
| 3,546,308 | 12/1970 | Moore | 585/352 |
| 3,551,514 | 12/1970 | Evering | 585/731 |
| 3,671,598 | 6/1972 | Moore | 585/350 |
| 3,689,590 | 9/1972 | Rakow et al. | 585/731 |
| 4,162,233 | 7/1979 | Kramer | 252/429 R |
| 4,229,611 | 10/1980 | Kramer | 585/728 |

OTHER PUBLICATIONS

"Industrial Laboratory Alkylation" edited by Lyle F. Albright and Arthur R. Goldsby, ACS Symposium Series 55, published Washington, D.C., 1977, Chapter One, Alkylation Studies, by George M. Kramer.
J. Org. Chem. 44, pp. 2619–2624, (1979), by D. Mirda, D. Rapp and G. M. Kramer.
J. Amer. Chem. Soc. 98, pp. 5864–5870, (1976), by P. Van Pelt and H. M. Buck.

Primary Examiner—Curtis R. Davis
Attorney, Agent, or Firm—Robert J. North

[57] ABSTRACT

A process is described for paraffin-olefin alkylation under strong acid conditions in which an aminoalkyladamantane hydrocarbon is used to substantially improve the reaction.

14 Claims, No Drawings

AMINOALKYL ADAMANTANE CATALYZED PARAFFIN-OLEFIN ALKYLATION

BACKGROUND OF THE INVENTION

This invention relates to a process for paraffin-olefin alkylation producing higher branched paraffins under strong, acid catalyzed conditions and in the presence of an aminoalkyladamantane hydrocarbon as a hydride transfer catalyst. The latter compound is preferably a surfactant in the acid system employed.

Alkylation of olefins by carbonium ions under strong acid conditions is a well-known process for producing a wide variety of useful hydrocarbon materials and particularly, gasoline blending components. For example, 2,2,4-trimethylpentane is a common blending component which is used for octane improvement of gasoline and it can be produced by alkylating isobutylene with t-butyl cations in sulfuric acid or liquid HF.

An example of an acid catalyzed reaction process is described in U.S. Pat. No. 3,231,633.

Hydrocarbon conversion processes employing novel Lewis acid systems are disclosed in U.S. Pat. Nos. 4,229,611 and 4,162,233, both assigned to Exxon Research and Engineering Company.

U.S. Pat. No. 3,671,598 describes a process for isomerizing saturated cyclic hydrocarbons under strong acid conditions in the presence of an adamantane hydrocarbon. However, no suggestion is made that it might be effective in paraffin-olefin alkylation nor that other specifically substituted adamantanes, particularly those with aminoalkyl substituents, might be more effective in increasing the rate of paraffin-olefin alkylation.

New methods for producing such alkylated paraffinic hydrocarbons useful as octane improvement agents are constantly being searched for in an effort to increase product quality and process efficiency. Improved processing should lower side reactions, leading to less catalyst consumption while increasing product quality (octane number), yield and reaction rate.

SUMMARY OF THE INVENTION

We have unexpectedly found that the presence of a surface active aminoalkyladamantane hydrocarbon in a strong acid system containing a paraffinic carbonium ion rapidly increases the rate of intermolecular hydride transfer for the paraffinic carbonium ion in the system. (These ions are typified by the t-butylcarbonium ion, $t-C_4H_9^{\oplus}$.) Since intermolecular hydride transfer is generally the rate determining step in paraffin-olefin alkylation, see "Industrial Laboratory Alkylation", edited by Lyle F. Albright and Arthur R. Goldsby, ACS Symposium Series 55, Published Washington D.C. 1977, Chapter one "Alkylation Studies" by G. M. Kramer) involving hydride transfer from a paraffin to an alkyl or paraffinic carbonium ion, the presence of the adamantane hydrocarbon will serve to significantly increase the reaction rate of the alkylation process. In the production of octane-increasing agents, this should lead to the formation of purer product quality due to higher selectivity, lower acid consumption, which is an environmental consideration, and higher yields, which enhances the economics of the process.

More specifically, by this invention, there is provided an alkylation process comprising contacting a $C_4-C_6$ linear or branched paraffinic compound, capable of forming a carbonium ion under strong acid conditions, with a $C_2-C_5$ olefin in the presence of a strong acid system and an aminoalkyladamantane hydrocarbon containing at least one unsubstituted bridgehead position at a temperature of about $-100°$ to $150°$ C., thereby producing a $C_6-C_{11}$ branched paraffinic hydrocarbon.

In the process, the total range of described applicable paraffins and olefins can be used in the subject paraffin-olefin alkylation under very strong acid conditions, e.g., $AlBr_3$. However, in the slightly weaker acid systems, such as $H_2SO_4$ and HF, ethylene and n-butane do not generally undergo the alkylation process and require the stronger acid systems as described herein.

DESCRIPTION OF THE INVENTION AND PREFERRED EMBODIMENTS

The reason that aminoalkyladamantane hydrocarbon serves to increase the rate of intermolecular hydride transfer during paraffin-olefin alkylation is not clearly understood. One theory that we do not wish to be bound by is that reversible hydride transfer from the adamantyl moiety to a carbonium ion in solution is enhanced due to lack of steric repulsions in the transition state involving adamantyl moiety, as compared to that involving a paraffinic hydrocarbon.

In the process, $C_2-C_5$ olefins are alkylated with $C_4-C_6$ linear or branched paraffinic compounds to produce effective gasoline octane improver agents. Preferably, the starting paraffinic compound is branched since branching facilitates reaction and usually results in a higher octane number product. Representative examples include n-butane, isobutane, n-pentane, isopentane, and isomeric hexanes and mixtures thereof. A preferred paraffin in the process is isobutane.

Carbonium ions in the process can be generated in various ways; in situ from their respective halides, by protonation of an olefin, or by oxidation of a paraffin by the acid system, or they can be generated from the free hydrocarbon undergoing intermolecular hydride transfer to carbonium ions already present in the acid. The preferred method depends on the acid system, but with $H_2SO_4$ or HF, they are formed readily by protonation of olefins.

Linear or branched $C_2-C_5$ olefins or cyclic olefins useful in the process include ethylene, propylene, butene-1, butene-2, isobutylene, cyclopentene, pentene-1, pentene-2, methylbutenes, mixtures thereof, and the like. Preferred olefins are butylenes and amylenes, as for example, feeds available in catalytic cracking streams. Particularly preferred are the butylenes.

The weight ratio of paraffin-olefin used in the process is generally about 5 to 1 and preferably about 10 to 1.

The product hydrocarbons in the reaction of isobutene with butylenes are mainly $C_8$ branched paraffins. Representative examples include 2,2,4-, 2,3,4-, 2,3,3-, and 2,2,3-trimethylpentanes, 2,4-, 2,3-, and 2,5-dimethylhexanes, and the like. Preferred products in the process are the trimethylpentanes. The products are useful as gasoline blending agents for octane improvement and/or hydrocarbon solvents.

The phrase "a strong acid system", as used herein, refers to an acid system capable of assisting in generating carbonium ions in the process and includes an "acid component" and a solvent, or a material that can function in both capacities, such as concentrated sulfuric acid or liquid HF. The acid system can be solid, liquid, gaseous or in vapor form. Preferably the acid system is a liquid.

The strong acid components in the acid system are conventional protic and aprotic or Lewis acids and include $AlBr_3$, $AlCl_3$, $GaCl_3$, $TaF_5$, $AsF_5$, $BF_3$, HF, HCl, HBr, $H_2SO_4$, $HSO_3F$, $CF_3SO_3H$, and the like, and mixtures thereof. Preferred acid components in the process are $H_2SO_4$, HF, $CF_3SO_3H$, or $HSO_3F$. It should be noted that HCl and HBr are preferably used in combination with other Lewis acids, e.g., $AlCl_3$ and $AlBr_3$.

Also, an ingredient in the "acid system" may be a solvent required for the acid component. For Lewis acids, halogenated paraffins and polyhalogenated aromatics are generally used; representative examples include, but are not limited to, $CH_3Br$, $CH_2Br_2$, $CH_2Cl_2$, 1,2-dichloroethane, 1,2,3-trichlorobenzene, 1,2,3,4-tetrachlorobenzene, pentafluorobenzene, HF, $H_2SO_4$, $HSO_3F$, $CF_3SO_3H$, and the like, and mixtures thereof.

The molar concentration of the Lewis acid in these solvents generally varies from 0.1 M to 5.0 M. Preferably the range is between 0.5 M and 2.0 M.

The volume ratio of the acid system to the paraffinic hydrocarbon is generally between 5/1 and 1/5 and preferably from 3/1 to 1/3. However, larger and smaller ratios can also be effectively used.

The aminoalkyladamantane hydrocarbon useful in the process contains at least one aminoalkyl group and at least one unsubstituted bridgehead position, is surface active and can be prepared by conventional methods in the art. By the term "surface active", is meant that the aminoalkyladamantane depresses the surface tension of the acid system when used at low concentrations.

The aminoalkyladamantane is preferably of the formula:

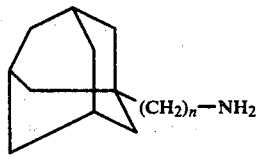

where $n = 0-10$, and wherein the adamantyl ring, the alkyl chain and the amino group can be further modified and substituted with groups which are inert under the process conditions. Suitable modifications include $C_1$-$C_4$ alkyl groups for the amino protons and $NO_2$ and $CF_3$ or $C_nF_{2n+1}$ ($n = 1 \ldots 10$) replacements for protons on the rest of the molecule, provided that at least one bridgehead hydrogen remains.

Representative examples include 4-aminobutyl-[1-adamantane], preferably, and 3-aminopropyl-[1-adamantane], 2-aminoethyl-[1-adamantane], and 1-aminoethyl-[1-adamantane] and 4-aminobutyl-[2-adamantane].

The molar concentration of aminoalkyladamantane in the acid solution varies from about $10^{-6}$ to $10^{-1}$ moles/liter, and preferably about $10^{-4}$ to $10^{-2}$ moles/liter. However, larger and smaller ratios can also be used effectively.

Temperatures in the process are conducted in the range of about $-100°$ to $150°$ C., and preferably about $-60°$ to $65°$ C., depending primarily on the temperature required to obtain a liquid phase catalyst being preferred.

The process is normally carried out at atmospheric pressure but may also be conducted at higher pressures up to about 20 atmospheres, the pressure depending primarily on the partial pressure of isobutane in the reaction mixture.

Yields of paraffinic branched hydrocarbons in the process range from about 80 to 100 percent of theory, based on starting olefin.

Particularly preferred embodiments of the process are where isobutylene is reacted with isobutane to produce predominantly a mixture of 224,234,233 and 223 trimethylpentanes, propylene is reacted with isobutane to produce a $C_7$ product comprising 2,3- and 2,4-dimethylpentanes; where isobutane is reacted with a mixture of butenes, as obtained from a petroleum feedstream, to produce a mixture comprising branched $C_8$ paraffinic hydrocarbons of which at least 80 percent are trimethylpentanes; and wherein isobutane is reacted with a mixture of amylenes, as obtained from a petroleum feedstream, to produce a mixture comprising predominantly branched $C_8$ and branched $C_9$ paraffinic hydrocarbons.

Apparatus for carrying out the subject process is conventional either on a laboratory, pilot plant, or full industrial scale and the process can be conducted in a batch-type operation or in a continuous-type operation and in a slurry, liquid, gaseous or vapor phase. Preferred type of process is one conducted in a continuous manner.

Generally, the process is conducted by contacting a liquid mixture of paraffin, olefin, and aminoalkyladamantane hydrocarbon with the acid system described herein. If the hydrocarbon mixture is miscible with said acid system, then the reaction takes place in a one-phase homogeneous manner. If the acid system is, for example, $H_2SO_4$, then the process is conducted in a two-phase manner, the acid system being the lower phase. The entire system is preferably at reaction temperature at time of mixing during which the entire system is adequately mixed, stirred and agitated to insure good contact between the acid system and the hydrocarbon system. The reaction is allowed to progress until a desired or substantial quantity of formed product is obtained. This can be monitored by analytical methods such as gas chromatography and mass spectrometry. After the desired paraffinic product has been formed, the phases can be separated and the hydrocarbon phase treated by extraction or fractional distillation, and the like, to separate out and collect the desired product.

It is to be understood that obvious modifications and variations on the above-described procedure and subject process, not specifically described herein, are deemed to be encompassed within the general scope and spirit of the application.

The following examples are illustrative of the best mode of carrying out the invention, as contemplated by me, and should not be construed as being limitations on the scope or spirit of the instant invention.

EXAMPLE 1

This example shows that hydride transfer is catalyzed by the presence of adamantane in a strong acid containing carbonium ions.

An aluminum bromide solution was prepared by weighing 0.534 grams, 0.002 moles, $AlBr_3$ (purified by sublimation), into an NMR tube. The tube was cooled to $-78°$ C. and then $CD_3Br$ was passed through a bed of $CaCl_2$ (drier), and condensed on the $AlBr_3$ to provide a half milliliter of a 4.0 molar solution. The mixture was warmed and shaken quickly to provide the solution for study.

The t-butyl cation-adamantane system was prepared in two ways. One was by adding t-butylbromide and adamantane to the acid mixture just before warming and shaking, and the other was by reversing the procedure and mixing 1-bromoadamantane with isobutane. The additive concentrations were 0.1 M in all cases and provided clear homogeneous solutions.

Nuclear magnetic resonance studies ('H) were done at −40° C. on a Varian 360-L spectrometer. Both solutions exhibited substantially identical spectra showing a sharp absorption band with a half width of ca. 4.3H for the butyl methyl groups and another sharp absorption band for adamantane's methylene protons. The methine, (tertiary or bridgehead) hydrogen atoms, which are the species being transferred as hydrides, are seen as a small broad band.

Solutions of the t-butyl cation with isopentane, norbornane and methylcyclopentane showed a much broader band for the half width of the butyl system, the FWHM being about an order of magnitude greater than before, (full width at half maximum height) indicating that much slower intermolecular hydride transfer was occurring in these systems than when adamantane was present.

Since intermolecular hydride transfer is a slow step in isobutane-olefin alkylation, it is reasonably believed that in a paraffin-olefin acid catalyzed alkylation process, such as between isobutane and isobutylene, the presence of adamantane or an adamantyl derivative will substantially increase the reaction rate and improve the process.

EXAMPLE 2

This example shows how a surface active adamantylalkylamine accelerates intermolecular hydride transfer at a sulfuric acid hydrocarbon interface and results in the faster isomerization of a branched paraffin (3-methylpentane to 2-methylpentane). Table I lists the surface tension of solutions of different molarity, M of 4-aminobutyl-[1-adamantane] in 95.9 percent $H_2SO_4$. Also shown are the isomerization rates of 3-methylpentane obtained under well-stirred conditions using equal volumes of hydrocarbon and acid. For comparison, the isomerization rates with no additive and with dodecylamine (a surfactant which cannot function as a hydride transfer intermediate) are also shown.

TABLE I

Isomerization of 3-Methylpentane in Conc. $H_2SO_4$, 25° C.

| Additive, M | Rate Constant, hr. | Rel. Rate | Surface Tension, dynes/cm. |
|---|---|---|---|
| None | 0.021 | 1.0 | 59.5 |
| AAB[(1)], 0.002 | 0.064 | 3.0 | 59.0 |
| AAB, 0.005 | 0.118 | 5.6 | 57.7 |
| AAB, 0.050 | 0.16 | 7.6 | 50.8 |
| $C_{12}H_{25}NH_2$, 0.050 | 0.040 | 1.9 | 44.5 |

[(1)]4-aminobutyl-1-adamantane = AAB.

The data indicate a sharp increase in the isomerization rate at the concentration at which AAB begins to depress the surface tension of the acid. The comparison between AAB and $C_{12}H_{25}NH_2$ indicates the value of incorporating hydride transfer capability into the surfactant.

Since the isomerization of 3-methylpentane in $H_2SO_4$ is believed to involve a slow, rate determining hydride transfer, this example indicates that AAB will catalyze this type of process in conc. $H_2SO_4$. Since this is believed to be a slow step in isobutane-olefin alkylation it is reasonable to believe that this process will similarly be improved by this type of surfactant.

What is claimed is:

1. An alkylation process comprising contacting a $C_4$–$C_6$ linear or branched paraffinic compound, capable of forming a carbonium ion under strong acid conditions, with a $C_2$–$C_5$ olefin in the presence of a strong acid system and an aminoalkyladamantane hydrocarbon containing at least one unsubstituted bridgehead position, at a temperature of about −100° to 150° C., thereby producing a $C_6$–$C_{11}$ branched paraffinic hydrocarbon.

2. The process of claim 1 wherein said paraffinic compound is selected from n-butane, isobutane, n-pentane, isopentane, n-hexane, isomers thereof, and mixtures thereof.

3. The process of claim 1 wherein said olefin is selected from ethylene, propylene, butene-1, butene-2, isobutylene, linear and branched pentenes, and mixtures thereof.

4. The process of claim 1 wherein said acid system contains an acid component selected from $AlBr_3$, $AlCl_3$, $GaCl_3$, $TaF_5$, $AsF_5$, $BF_3$, HF, HBr, HCl, $H_2SO_4$, $HSO_3F$, $CF_3SO_3H$, and mixtures thereof.

5. The process of claim 4 wherein said acid component is HF, $H_2SO_4$, $HSO_3F$, or $CF_3SO_3H$.

6. The process of claim 4 wherein said acid system further contains a solvent selected from $CH_3Br$, $CH_2Br_2$, $CH_2Cl_2$, 1,2-dichloroethane, 1,2,3-trichlorobenzene, 1,2,3,4-tetrachlorobenzene, pentafluorobenzene, HF, $H_2SO_4$, $HSO_3F$, $CF_3SO_3H$, and mixtures thereof.

7. The process of claim 1 wherein said aminoalkyladamantane is of the formula:

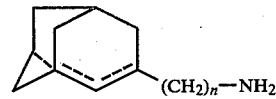

where n=0–10, and the adamantane ring, alkyl chain and amino group can be substituted with substituents which are inert or unreactive under the process conditions.

8. The process of claim 7 wherein said aminoalkyladamantane is 4-aminobutyl-1-adamantane.

9. The process of claim 1 wherein said temperature is in the range of about −60° to 65° C.

10. The process of claim 1 being conducted in a continuous manner.

11. The process of claim 1 wherein said paraffinic compound is isobutane, said olefin is isobutylene and said product is predominantly a mixture of 2,2,4-, 2,3,4-, 2,2,3- and 2,3,3-trimethylpentane.

12. The process of claim 1 wherein said paraffinic compound is isobutane, said olefin is propylene and said $C_7$ product is predominantly a mixture of 2,3- and 2,4-dimethylpentanes.

13. The process of claim 1 wherein said paraffinic compound is isobutane, said olefin is a mixture of butenes and said product is an alkylate, comprising $C_8$ hydrocarbons of which trimethylpentanes are at least 80 weight percent.

14. The process of claim 1 wherein said paraffinic compound is isobutane, said olefin is a mixture of amylenes, and said product comprises a mixture of branched $C_8$ and $C_9$ paraffinic hydrocarbons.

* * * * *